(12) United States Patent
Basini et al.

(10) Patent No.: US 7,829,753 B2
(45) Date of Patent: Nov. 9, 2010

(54) CATALYTIC SYSTEM FOR THE PRODUCTION OF OLEFINS

(75) Inventors: Luca Basini, Milan (IT); Domenico Sanfilippo, Paullo (IT); Alessandra Guarinoni, Piacenza (IT)

(73) Assignee: Saipem S.p.A., San Donato Milanese (IT)

( * ) Notice: Subject to any disclaimer, the term of this patent is extended or adjusted under 35 U.S.C. 154(b) by 0 days.

(21) Appl. No.: 12/033,572

(22) Filed: Feb. 19, 2008

(65) Prior Publication Data

US 2008/0139862 A1     Jun. 12, 2008

Related U.S. Application Data

(63) Continuation of application No. 11/561,092, filed on Nov. 17, 2006, now abandoned, which is a continuation of application No. 10/359,191, filed on Feb. 6, 2003, now abandoned.

(30) Foreign Application Priority Data

Feb. 6, 2002     (IT) ........................... MI2002A0214

(51) Int. Cl.
*C07C 5/42* (2006.01)
*B01J 27/24* (2006.01)
(52) U.S. Cl. ...................... 585/658; 585/660; 502/200; 423/385; 423/400; 423/406; 423/409

(58) Field of Classification Search .................. 502/200; 423/385, 400, 406, 409; 585/658, 660
See application file for complete search history.

(56) References Cited

U.S. PATENT DOCUMENTS

| 4,940,684 | A | 7/1990 | Okutani et al. |
| 5,444,173 | A | 8/1995 | Oyama et al. |
| 5,935,897 | A | 8/1999 | Truebenbach et al. |
| 6,479,027 | B1 | 11/2002 | Jacobsen |
| 2003/0013605 | A1 | 1/2003 | Klassen et al. |

FOREIGN PATENT DOCUMENTS

| CA | 2 395 925 A1 | 7/2001 |
| DE | 100 02 117 A1 | 8/2001 |
| EP | 0266875 | 5/1988 |
| EP | 0 775 519 | 5/1997 |
| GB | 2 297 043 | 7/1996 |
| JP | 04118052 A | 4/1992 |

OTHER PUBLICATIONS

U.S. Appl. No. 12/271,371, filed Nov. 14, 2008, Basini, et al.

*Primary Examiner*—Elizabeth D Wood
(74) *Attorney, Agent, or Firm*—Oblon, Spivak, McClelland, Maier & Neustadt, L.L.P.

(57) ABSTRACT

Catalytic system for partial oxidation reactions of hydrocarbons characterized in that it contains:
    one or more metals belonging to the $1^{st}$, $2^{nd}$, and $3^{rd}$ transition series;
    one or more elements of group IIIA, IVA or VA,
wherein at least one of said metals or said elements is in the form of a nitride.

17 Claims, 1 Drawing Sheet

CATALYTIC SYSTEM FOR THE PRODUCTION OF OLEFINS

Figure 1A:
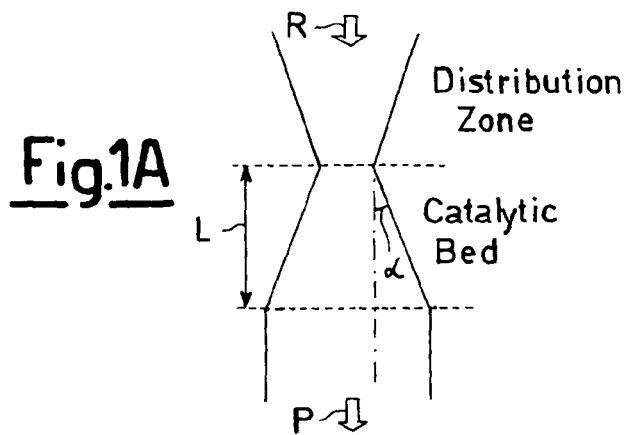

The present invention relates to a catalytic system for the production of olefins by means of a partial oxidation process of saturated hydrocarbons such as ethane, propane, isobutane and naphtha. The catalytic system and the reactor solutions described provide the possibility of effecting the partial oxidation reactions of saturated hydrocarbons to olefins also with a low contact time, at a high temperature and high pressure.

The main reaction on which the process is based is the following:

$$C_nH_{2n+1}-CH_2CH_2-C_mH_{2m+1}+0.5O_2 \rightarrow C_nH_{2n+1}-CH=CH-C_mH_{2m+1}+H_2O \quad [1]$$

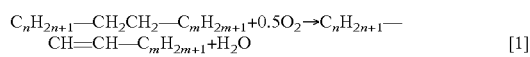

Olefins have various uses in the production field of polymers (for example, polyethylene, polypropylene), copolymers (for example, synthetic rubbers), plastic materials (for example, vinyl plastics), basic chemical products (for example, ethylene oxide, propylene oxide, cumene and acrolein) and high-octane products (for example, methyl tertbutyl ether).

Olefins are industrially produced by means of non-catalytic steam cracking processes and fluid bed or mobile bed or fixed bed catalytic dehydrogenation processes.

Steam cracking is the most widely-used process for producing low molecular weight olefins such as ethylene and propylene and can treat mixed charges of hydrocarbons such as naphtha. Steam cracking processes can be divided into three zones where the following operations take place:
- dehydrogenation reactions of hydrocarbons and the formation of olefins (hot zone)
- compression of the reaction products
- separation of the reaction products (cold zone)

The chemical reactions in the steam cracking processes are pyrolysis reactions which are effected at high temperatures by passing a stream of saturated hydrocarbons and steam inside coiled tubes inserted in an oven.

The formation reactions of olefins [2]

$$C_nH_{2n+2} \rightarrow C_nH_{2n}+H_2 \quad [2]$$

are highly endothermic and the process requires in relation to the charge used, from 1.6 to 2.8 mJ/kg of product.

The residence times of the gaseous stream of the reagents inside the tubes typically vary from 0.1 to 0.15 sec. but there are also technologies which use residence times of a few milliseconds.

The inlet temperatures of the tubes range from 500-700° C., whereas those at the outlet are within the range of 775-950° C.

The reaction zone of the plants is modular. The modules have a capacity of about 100,000 tons/year; as a whole world-scale plants have a capacity which is even higher than 750,000 tons/year.

The heat necessary for the steam cracking reactions is produced by burning hydrocarbons; this causes strong emissions of $CO_2$ and $NO_x$ which in many countries must be separated before the fumes are released into the atmosphere.

Steam cracking also requires the presence of vapour (30-50% in the feeding) which decreases the partial hydrocarbon pressure and reduces coke formation reactions.

In spite of the presence of vapour, periodical decoking operations of the plants are necessary. The modular nature of the plants allows these operations to be cyclically effected without interrupting the production.

Only 35-50% of the heat produced by the burners is transferred to the reagent mixture; thermal recovery and vapour generation systems, however, increase the overall thermal efficiency of the process.

In the case of the production of ethylene, the yields vary from 50 to 60% on a molar basis depending on the charges used. Starting from ethane, the yields can range from 57-60% on a molar basis, with conversion values of ethane which can reach 67% and selectivity values to ethylene which can reach 83%.

Catalytic dehydrogenation processes are mainly used for the production of propylene, butenes and pentenes from pure charges of propane, isobutane, butane and isopentane (F. Buonomo, D. Sanfilippo, F. Trifiro, Dehydrogenation Reactions in: "Handbook of Heterogeneous Catalysis", Vol. 5, pages 2140-2151, G. Ertl, H. Knozinger, J. Weitkamp Eds. VCH Verlagsgesellschaft mbH, Weinheim).

Industrial catalytic dehydrogenation processes are mainly based on three groups of materials consisting of:
- supported noble metals, mainly represented by Pt/Sn systems,
- supported chromium oxides
- mixed oxides such as molybdenum and vanadium oxides.

Systems consisting of Pt/Sn and alkaline metals are used in the Oleflex technology of UOP and the STAR technology of Phillips (D. H. James, W. M. Castor, Ullmann's Encycl. Ind. Chem. 5$^{th}$ Ed. 1994, Vol. 25, pages 329-344). Systems based on chromium oxide are used in the Catofin technology of UCI-ABB Lummus and FBD technology of Snamprogetti-Yarsintez.

The reactor solutions used in catalytic dehydrogenation technologies comprise a reaction step in which the dehydrogenation of the hydrocarbon takes place, and a regeneration step of the catalyst consisting of a combustion process of the carbonaceous residues accumulated in the reaction step.

More specifically, the reaction solutions used comprise:
- fixed bed adiabatic reactors (Catofin technology of Lummus) which operate with rapid reaction and regeneration cycles; wherein the regeneration cycle has the double function of burning the carbon accumulated during the reaction and supplying the heat for the subsequent dehydrogenation reactions (F. Trifiro, F. Cavani, Oxidative Dehydrogenation and Alternative Dehydrogenation Processes Catalytica Studies Division Mountain View Calif., USA 1993 Study Number 41920D)
- mobile bed adiabatic reactors (Oleflex technology of UOP) between which the catalyst is moved and heated and finally sent to a regeneration step in which the carbonaceous residues are burnt (P. R. Pujado, B. V. Vora Hydroc. Process 1990, 65)
- fixed bed multi-tubular reactors inserted in ovens analogous to those of steam reforming processes in which various blocks are used alternatively in reaction and regeneration cycles (STAR technology of Phillips, R. O. Dunn, G. F. Schuette, F. M. Brinkmeyer, W. Sund, Proc. De Witt Petrochem. Review Houston 1991, 1)
- fluid bed reactors in which the catalyst circulates continuously between a regeneration and reaction reactor conveying the heat necessary for the dehydrogenation (FBD technology of Snamprogetti-Yarsintez, D. Sanfilippo, F. Buonomo, G. Fusco, M. Lupieri, I. Miracca Che. Eng. Sci. 1992, 47, 2313).

The energy requirements of the reactions and necessity for transferring heat to the reactions are largely responsible for the investment costs and energy consumption of the "hot" section of steam cracking technologies and catalytic dehydrogenation technologies.

An alternative method to that so far applied for the production of ethylene consists of partial oxidation reactions, also called oxidative dehydrogenation [3].

$$C_nH_{2n+2} + \tfrac{1}{2}O_2 \rightarrow C_nH_{2n} + H_2O \qquad [3]$$

These reactions are moderately exothermic, they have a low selectivity towards carbonaceous products and can be carried out in adiabatic reactors.

This method has been studied in depth, but since 1992 good yields of olefinic products have not been obtained (F. Trifiro, F. Cavani, Oxidative Dehydrogenation and Alternative Dehydrogenation Processes Catalytica Studies Division Mountain View Calif., USA 1993 Study Number 41920D).

In 1992, L. D. Schmidt et Al. at the University of Minnesota discovered reaction conditions and catalysts which allowed the production of yields to ethylene comparable to those of steam cracking processes and to propylene higher than those of catalytic processes.

The reactions are carried out with a low contact time ($\approx 10$ ms) and produce olefins from mixtures of the corresponding saturated alkanes and oxygen/air.

The results obtained are described in numerous articles in scientific literature (M. Huff, L. D. Schmidt J. Phys. Chem. 1993, 97, 11815; M. Huff and L. D. Schmidt, J. Catal. 1994, 149, 127; C. Yokoyama S. S. Bharadwaj and L. D. Schmidt, Catalysis Lett. 1996, 38, 181; A. S. Bodke, D. A. Olshki, L. D. Schmidt E. Ranzi, Science 1999, 285, 712; A. S. Bodke, D. Henning, L. D. Schmidt, S. S. Bharadwaj, J. J. Maj, J. Siddal, J. Catal. 2000, 191, 62).

Basic studies were followed by studies on technological applications which generated patents and patent applications. The University of Minnesota, Dow Chemical Company and BP-Amoco are the most active organizations in this field.

In WO-96/13475 assigned to the University of Minnesota, the production reactions of olefins with a low contact time are effected using platinum compounds supported on ceramic foamy monoliths consisting of oxides selected from those of Al, Zr, Ca, Mg, Hf and/or Ti.

U.S. Pat. No. 5,639,929 of the University of Minnesota claims a partial oxidation process of hydrocarbons to mono-olefins effected in a fluidized bed using a catalyst selected from Pt, Rh, Ni and Pt—Au deposited on a carrier in the form of particulate.

U.S. Pat. No. 5,905,180 of the University of Minnesota claims a partial oxidation process for the production of mono-olefins from paraffins with a catalyst consisting of Pt and Sn deposited on a foamy ceramic carrier.

In U.S. Pat. No. 6,072,097 of the University of Minnesota, the production reactions of mono-olefins are obtained with catalysts consisting of Pt and Sn or Pt and Cu supported on a foamy ceramic monolith.

WO-00/14035 of Dow Chemical Company claims a catalytic partial oxidation process for the production of olefins effected by putting paraffins, oxygen and hydrogen in contact with each other. The patent also claims the possibility of carrying out the reactions in a fluid bed reactor.

WO-00/14180 of Dow Chemical Company claims a partial oxidation process of hydrocarbons with an autothermal process in the presence of a catalyst comprising at least one metallic promoter supported on a fibrous monolithic carrier in which the presence of hydrogen together with oxygen and hydrocarbon is recommended. The patent also claims a method for regenerating the catalyst during the reaction conditions.

WO-00/37399 of BP Chemical Ltd. claims a production and separation process of olefins by means of the partial oxidation of hydrocarbons comprising a partial oxidation passage of hydrocarbons and a separation step by means of an interaction with a solution of a metallic salt capable of selectively absorbing the olefins.

WO-00/14036 of BP Chemical Ltd. claims a catalytic process for the production of olefins by means of the partial oxidation of hydrocarbons carried out in various steps. In a first step, combustion reactions are effected which do not completely use up the oxygen; in a second step with a second catalyst, the combustion products and the non-reacted oxygen are interacted with the other saturated hydrocarbon causing the total consumption of the oxygen and olefins.

Finally, WO-00/15587 of BP Chemical Ltd. claims a catalytic process for the production of olefins and synthesis gas by means of the partial oxidation of hydrocarbons.

In short, the documents of scientific literature and patents mentioned above describe oxidative dehydrogenation processes carried out with a low contact time both in fluid bed reactors and fixed bed reactors. The catalysts described mainly contain Pt and a second metal such as Sn or Cu deposited on a ceramic carrier such as a foamy monolith. The patents also describe the possibility of effecting the oxidative dehydrogenation of mixtures of hydrocarbon reagents, oxygen and hydrogen. The latter gas allows an improvement in the selectivities of the reactions reducing the contributions of oxidations to CO, $CO_2$ and $H_2O$.

The use of premixed streams of hydrocarbons, oxygen and hydrogen however creates problems relating to safety particularly when the premixed streams are within flammability and explosivity curves (as in the case of the mixtures described in the documents of literature mentioned above).

Furthermore, due to the high reagent flows, the catalytic beds must be filled and have such dimensions as to allow low pressure drops, with the consequent use, in most of the experiments described in literature, of fluid beds or catalytic beds consisting of monoliths.

The great increase in temperature and the increase in the number of reaction moles [2] may be a further cause of a pressure drop inside the catalytic bed. The pressure drop can be limited by an increase in the total pressure, but this increase favours radicalic reactions in gaseous phase which form by-products with a high C/H ratio and in particular carbonaceous residues which deactivate the catalysts.

Finally, strong changes in temperature and high reaction temperatures can increase the fragility of the ceramic monoliths and ceramic pellets making them crumble and can also cause a loss in active metals such as Pt and Sn.

A catalytic system has now been found, which has an exceptional thermal, chemical and mechanical stability and provides the possibility of carrying out partial oxidation reactions of saturated hydrocarbons to olefins also with a low contact time, at a high temperature and high pressure.

The catalytic system, object of the present invention, for catalytic partial oxidation reactions of hydrocarbons is characterized in that it contains:

one or more metals belonging to the $1^{st}$, $2^{nd}$ and $3^{rd}$ transition series, preferably selected from Pt, Cr, V, Mo, W, Cu, Ru, Zn, Ag, Au, Rh, Mn, Fe, Co and Ni;

one or more elements of group IIIA, IVA or VA, preferably selected from Sn, Ga, Pb, Sb, Bi, Si, wherein at least one of said metals or said elements is in the form of a nitride.

With the definite presence of at least one nitride, the metal (or metals) belonging to the $1^{st}$, $2^{nd}$ or $3^{rd}$ transition series can be in the catalytic system in the form of a nitride (as counter-ion of the nitride or oxy-nitride) and/or deposited, in a quantity preferably ranging from 0.05 to 15% by weight, with respect to the nitride or oxy-nitride, whereas the element (or elements) of group IIIA, IVA or VA can be in the catalytic system in the form of a nitride (as counter-ion of the nitride or oxy-nitride) and/or deposited, in a quantity preferably ranging from 0.05 to 15% by weight, with respect to the nitride or oxy-nitride.

Some nitrides of transition metals have intrinsic catalytic properties, others can be used as carriers of metallic species with catalytic properties such as, for example, bimetallic or trimetallic systems (i.e. where there are two or three metals deposited on the nitride or on the oxy-nitride) preferably selected from the combinations Pt—Sn, Pt—Ga and Pt—Cu and the combinations Pt—Sn—Cr, Pt—Sn—Ga, Pt—Sn—Bi and Pt—Sn—Sb, respectively.

In particular, the following nitrides can be mentioned, consisting of:

- AlN, CO$_3$N, Cr$_2$N, Fe$_4$N, Mn$_4$N, MoN, TiN, WN, VN, Si$_3$N$_4$ (for example described in: F. K. Van Dijen, A. Kerbr, U. Voigt, W. Pfeiffer, M. Schulze, in "Key Engineering Materials" Vols. 89-91, M. J. Hofmann P. F. Becher and G. Petzow Eds. TransTech. 1994, pages 19-28; H. Lange, G. Wotting H. Winter, *Angew. Chem.* 1991, 103, 1606)
- Si—N—B systems or Si—B—N—C systems such as Si$_3$B$_3$N$_7$ and SiBN$_3$C (H. P. Baldus and M. Jansen, Angew. Chem. Int. Ed. Engl. 1997, 36, 328)
- systems consisting of layers of aluminum nitrides deposited on oxide carriers by means of atomic layer epitaxy or chemical vapour deposition (M. E. Bartram, T. A. Michalske, J. W. Rogers, T. M. Mayer Chem. Mater. 1991, 3, 353; M. E. Bartram, T. A. Michalske, J. W. Rogers, R. T. Paine, Chem. Mater., 1993, 5, 1424; C. Soto, V. Boiadjiev, W. T. Tysoe, Chem. Mater. 1996, 8, 2359)
- oxy-nitride systems described in P. W. Lednor and R-de Ruter, J. Chem. Soc. Chem. Comm. 1991, 1625

The above materials are representative but non-limiting of the group of nitrides which can be used, as the only limitations relate to stability under the reaction conditions.

The above systems in fact have proved to have considerable resistance to the thermal and mechanical stress which is produced during the start up reactions and shutdown of the reactions and also have a high thermal stability under the reaction conditions particularly at temperatures higher than 1000° C.

The nitrides AlN, CO$_3$N, Cr$_2$N, Fe$_4$N, Mn$_4$N, MoN, Si$_3$N$_4$, TiN, WN, VN, can be prepared for example by means of the reactions [4-7] (as described in The Chemistry of Transition Metal Carbides and Nitrides, S. T. Oyama Ed., Blackie Academic Professional, Glasgow, 1996).

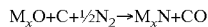

$$M_xO + C + \tfrac{1}{2}N_2 \rightarrow M_xN + CO \quad [4]$$

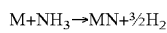

$$M + NH_3 \rightarrow MN + \tfrac{3}{2}H_2 \quad [5]$$

$$M_xO + NH_3 \rightarrow M_xN + H_2O + \tfrac{1}{2}O_2 \quad [6]$$

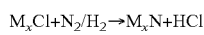

$$M_xCl + N_2/H_2 \rightarrow M_xN + HCl \quad [7]$$

wherein M=Al, Cr, Ti, V, Mo, Mn, Co, Fe, W

Bimetallic nitrides containing transition metals of groups VIB and VIII can be prepared according to reaction [8] as described in EP 1036592; C. J. H. Jacobsen, Chem. Comm. 2000, 1057

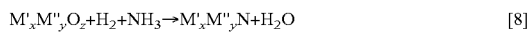

$$M'_xM''_yO_z + H_2 + NH_3 \rightarrow M'_xM''_yN + H_2O \quad [8]$$

Whereas Si—N—B systems or Si—B—N—C systems such as Si$_3$B$_3$N$_7$ and SiBN$_3$C are prepared as described in P. Baldus, M. Jansen, D. Sporn, Science 1999, 285, 699 according to the reactions:

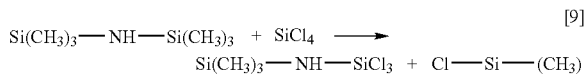

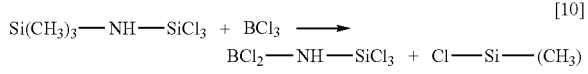

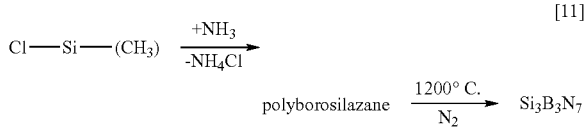

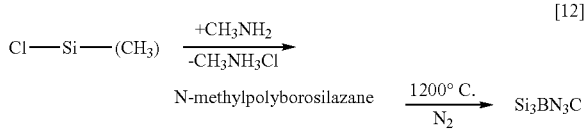

Systems consisting of layers of aluminum nitrides deposited on oxide carriers (for example Al$_2$O$_3$) can, on the other hand, be obtained by means of consecutive adsorptions of aluminum alkyls (for example Al(CH$_3$)$_3$) and ammonia on oxide surfaces so as to obtain the reaction [13] with a method described for example in: A. Dabrowski "Adsorption and its application in industry and environmental protection, Studies in Surf. Sci. and Catalysis 1999, 120A, 715; C. Soto, V. Bojadjiev, W. T. Tysoe Chem. Mater. 1996, 8, 2359.

$$Al(CH_3)_3 + NH_3 \rightarrow AlN + 3CH_4 \quad [13]$$

A further object of the present invention relates to a process for the production of olefins from gaseous paraffinic hydrocarbons, having from two to six carbon atoms, comprising a partial oxidation of said hydrocarbons with a gas containing molecular oxygen in the presence of the catalytic system specified above.

The partial oxidation is preferably effected at a temperature ranging from 450 to 1000° C., at a pressure ranging from 1 to 15 Atm and a space velocity ranging from 5000 to 800000 h$^{-1}$.

It has also been found that the process described above using the catalytic system according to the invention can give excellent results when it is carried out using tubular reactors in which the gas inlet zone and catalytic zone have a tubular shape, or reactors with a varying diameter in the gas distribution direction, in which the gas inlet zone and catalytic zone have a sand-glass or truncated-conical shape (see IT-MI96A000690).

These reactors with a varying diameter give the possibility of accelerating/decelerating the gaseous streams of the reagents and products.

This allows a reduction in the pressure drops as a result of the increase in temperature and volume caused by the reactions and also a reduction in the transmission of the reaction heat to the premixed reagent streams.

These characteristics are particularly advantageous if the reactions for the production of olefins are carried out at super-atmospheric pressures.

The possibility of effecting dehydrogenation reactions at super-atmospheric pressures is a great advantage with respect to the known technologies as it reduces the costs and consumption relating to the compression of the mixture of products before entering the separation cycle.

As far as the reactor design is concerned, the gas inlet zone and catalytic zone can either have a tubular shape, a sand-glass shape or a truncated-conical shape: the geometry is defined so as to maintain the surface rate values above the flame speed and contact times lower than the ignition delay in the zone prior to the catalytic bed and allow expansion of the product mixture, thus avoiding pressure drops, after the reactions have been activated.

The functions of the reagent gas inlet and distribution zone are therefore:
- to act as a barrier for the spreading of the radicalic reactions towards the feeding inlet, by the acceleration of the fluid and also by the presence of inert surfaces, capable of capturing the radicals
- to uniformly distribute the fluid on the inlet area in the catalytic bed (FIG. 1A), whereas the functions of the catalytic bed are:
- to activate oxidation reactions with mixtures which move at a high linear rate
- to follow the expansion of the fluid due to the increase in the number of moles and temperature without causing high pressure drops
- to maintain a surface rate in the whole of the bed which is higher than the critical value for producing flames and carbon black.

A further object of the present invention relates to a process carried out using reactors in which the inlet zone and catalytic zone have a tubular shape or a sand-glass shape or a truncated-conical shape, with the particular characteristic of sending into the gas inlet zone a stream of oxygen, air or enriched air and a fuel, not having the function of directly producing olefins, preferably selected from natural gas, synthesis gas, hydrogen or a mixture of hydrogen and CO, and in the catalytic zone a gaseous stream of paraffinic hydrocarbons.

This process carried out by feeding two types of fuel in different points can also be used with different catalysts from those claimed in the present patent application.

As already mentioned, the gas increases in volume due to the increase in temperature and stoichiometry of the reactions and is overheated by temperature values ranging from 80 to 600° C., preferably 100-400° C., in the distribution zone and ranging from 600 to 1300° C., preferably from 700 to 950° C. in the reaction zone.

The differential filling of the catalytic bed with particles having an increasing diameter along the gas distribution direction can also be used to reduce pressure drops.

One of the solutions adopted therefore consists of a filling of catalyst particles with an increasing diameter along the gas distribution direction.

A further innovative aspect relates to the possibility of using not only various geometries but also different catalysts in different reaction zones.

In particular, in reactors having a tubular or sandglass or truncated-conical shape, the catalyst fillings are differentiated so as to preferably have two or three catalytic beds in series.

In the case of two catalytic beds in series it is preferable to use catalytic systems consisting of:
- Pt deposited on nitrides or on oxy-nitrides in the bed upstream and Pt and Sn deposited on nitrides or oxynitrides in the bed downstream;
- Pt and Cu deposited on nitrides or on oxy-nitrides in the bed upstream and Pt, Sn and Ga deposited on nitrides or oxy-nitrides in the bed downstream;
- Pt and Ni deposited on nitrides or on oxy-nitrides in the bed upstream and Pt, Sn and Cr deposited on nitrides or oxy-nitrides in the bed downstream.

In the case of three catalytic beds in series, it is preferable to use catalytic systems consisting of:
- Pt deposited on nitrides or on oxy-nitrides in the bed upstream, Pt and Sn deposited on nitrides or oxynitrides in the intermediate bed and Pt, Sn and Ga deposited on nitrides or oxy-nitrides in the bed downstream;
- Pt and Cu deposited on nitrides or on oxy-nitrides in the bed upstream, Pt, Sn and Bi deposited on nitrides or oxy-nitrides in the intermediate bed and Pt, Sn and Ga deposited on nitrides or oxy-nitrides in the bed downstream;
- Pt deposited on nitrides or on oxy-nitrides in the bed upstream, Pt and Sn deposited on nitrides or oxynitrides in the intermediate bed and Pt, Sn and Sb deposited on nitrides or oxy-nitrides in the bed downstream;
- Pt and Cu deposited on nitrides or on oxy-nitrides in the bed upstream, Pt, Sn and Cr deposited on nitrides or oxy-nitrides in the intermediate bed and Pt, Sn and Ga deposited on nitrides or oxy-nitrides in the bed downstream;
- Pt and Ni deposited on nitrides or on oxy-nitrides in the bed upstream, Pt and Sn deposited on nitrides or oxy-nitrides in the intermediate bed and Pt, Sn and Ga deposited on nitrides or oxy-nitrides in the bed downstream.

The differentiated use of catalysts with different intrinsic activity characteristics allows selective combustion reactions to be effected in the zone downstream of the distribution zone and selective dehydrogenation reactions to olefins to be effected in the subsequent zone.

Figure 1B:
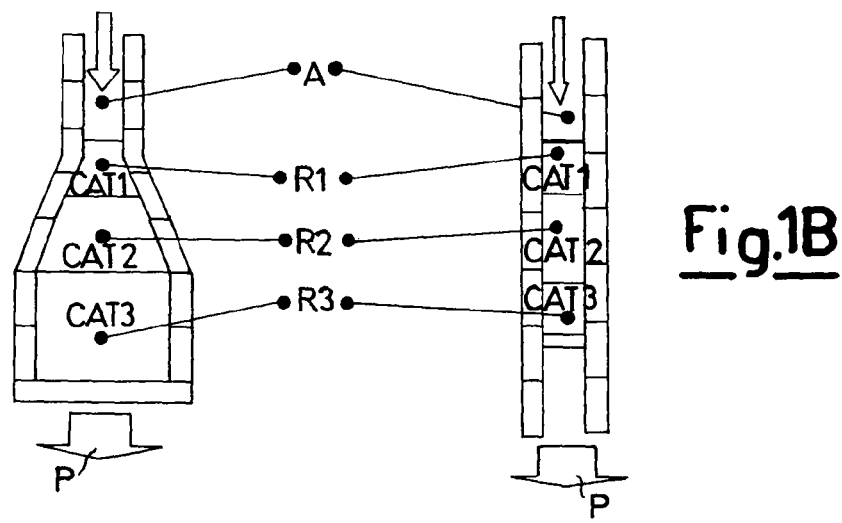
Figure 1C:
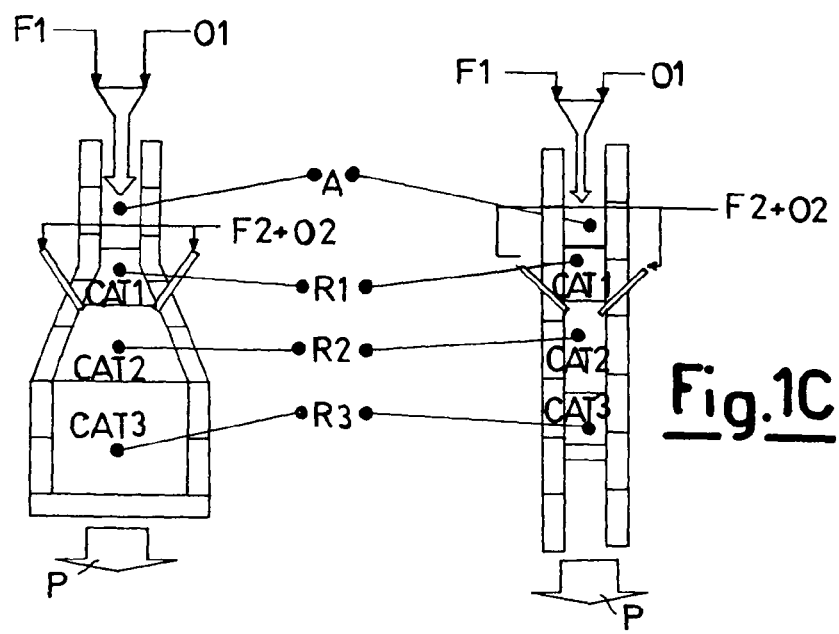

Two preferred embodiments of the reactors which can be used are provided hereunder with the help of FIGS. 1A, 1B and 1C.

With reference to FIG. 1A (in which the geometrical characteristics of the gas inlet and distribution zone and catalytic zone are schematized), the $\alpha$ values range from $0° \leq \alpha \leq 89°$. The value of the angle $\alpha$ and distance L are selected so as to:
- allow the expansion of the reaction gas avoiding pressure drops inside the catalytic bed and consequently prevent the spreading of flames countercurrent;
- leave the catalytic zone with a complete conversion of the oxygen molecules.

FIG. 1B schematizes a reactor with a varying diameter in the direction of the gas distribution and a tubular reactor.

In both reactors there is an inlet zone (A) of pre-mixed reagents and three catalytic zones (R1, R2 and R3) with differentiated fillings (CAT1, CAT2 and CAT3).

In FIG. 1C a reactor with a varying diameter in the direction of the gas distribution and a tubular reactor are schematized.

In both reactors there is a first inlet zone (A) of premixed reagents containing oxygen or air or enriched air (O1) and a fuel (F1) which can consist of natural gas or hydrogen or synthesis gas or any other fuel which does not have the function of directly producing olefins.

The combustion of this mixture is effected in a first reaction zone (R1) and has the function of producing the heat and reagents which favour dehydrogenation reactions, in a second reaction zone (R2), of a second hydrocarbon reagent (F2) which can consist of ethane, propane, butane or a liquid hydrocarbon such as naphtha or any other reagent which must be transformed into an olefinic compound.

Three different types of catalysts (CAT1, CAT2, CAT3) are used in different zones of the two reactors.

EXAMPLE 1

Comparative

The catalytic materials were tested in a quartz tubular reactor, with an internal diameter equal to 15 mm.

Fragments of monolith (upstream) and a ceramic monolithic foam (downstream) for a thermal shield for the catalytic bed; the monolith is welded to the reactor by means of ceramic paper in order to avoid the by-pass of the reagent gases and also acts as a support for the catalyst.

The reactor was positioned in an oven, with the double objective of preheating the reagents and reducing the loss in heat of the system.

Two thermocouples, at the beginning and at the end of the catalytic bed, co-axially positioned with respect to the distribution direction of the reagents/products, allowed the temperature of the gases at the inlet and outlet of the catalytic bed to be monitored.

The tests were carried out at a pressure slightly higher than the atmospheric value (1.3-1.5 bars), feeding ethane, nitrogen (15% v/v of reagent gases), oxygen and hydrogen.

The ethane/oxygen ($C_2H_6/O_2$) and hydrogen/oxygen ($H_2/O_2$) ratios were varied so as to obtain a correlation between the operating conditions and reactivity. The space velocity (GHSV, expressed in NL/kg/h) was maintained at 40.000 to 600.000.

The mixture of products was analyzed via gaschromatography; an online paramagnetic detector also allowed the possible presence of oxygen in the outgoing stream to be monitored and also facilitated the start-up/shutdown operations.

In this first example (comparative) the reactor was charged with a catalyst (indicated with the abbreviation PS7AL2 in Table 1) in which the carrier consisted of α-alumina pellets (more or less spherically shaped, with a particle diameter—$d_p$—equal to 1.2 mm). A commercial hydrochloric solution of Pt salts ($H_2PtCl_6$) and Sn salts ($SnCl_2.4H_2O$), was dripped onto the carrier, so as to give a weight percentage of Pt equal to 2 and an atomic ratio Sn:Pt equal to 7:1.

The operating conditions and results of the tests are summarized in Table 1; Examples 1A-D, ordered according to an increasing selectivity to ethylene, relate to different ethane/oxygen, hydrogen/oxygen ratios and space velocities: each condition was tested for at least 100 h.

EXAMPLE 2

A group of catalytic materials object of the present invention was tested in the same experimental apparatus and under analogous operating conditions to those described in Example 1 (comparative).

These materials are based on Pt and Sn (atomic ratio 1:7, 2% by weight of platinum) and were obtained with the same experimental procedure described in Example 1 using, instead of alumina, pellets of $Si_3N_4$ ($d_p$=1.5 mm).

The abbreviations PS7SN1, PS7SN3 and PS7SN4 refer to the same catalyst, obtained in different batches.

The analytic method used is the same as that described in Example 1 (Comparative).

The operating conditions and results of the tests are summarized in Table 2; examples 2A-F, ordered according to an increasing selectivity to ethylene, relate to different ethane/oxygen, hydrogen/oxygen ratios and space velocities: each condition was tested for at least 100 h.

EXAMPLE 3

The catalytic materials already described in Example 2 were alternatively tested in a quartz reactor consisting of a distribution zone and a catalytic zone, both conical (sand-glass configuration). The distribution zone has an inlet diameter of 15 mm and a height of 10 mm. The catalytic zone has an inlet diameter of 4 mm, a height of 18 mm and an outlet diameter of 20 mm.

The catalytic pellets were positioned between two zones filled with ceramic material acting as a thermal shield.

Two thermocouples, positioned longitudinally at the inlet and outlet of the catalytic bed, monitored the temperature of the gases at the inlet and outlet.

Also in this case, the reactor was positioned in an oven, with the double objective of preheating the reagents and reducing the loss of heat of the system.

The tests were carried out at a slightly higher pressure than atmospheric value (1.3-1.5 bars).

The analysis section is the same as that described in Example 1.

The gases fed in Examples 3A and 3B were ethane, nitrogen (percentage equal to 15% v/v approx.), oxygen and hydrogen. In Example 3C (carried out at a very low space velocity and with a greater volume of catalyst), a mixture of hydrogen and carbon monoxide was fed, in addition to ethane and oxygen.

The tests were carried out with the same batch of catalyst (PS7SN1) already defined in Example 2.

The operating conditions and results of the tests are summarized in Table 3; examples 3A-3B were obtained with the same ethane/oxygen ratio, and with different hydrogen/oxygen ratios and space velocities, whereas example 3C, in which a mixture of Co and hydrogen was fed, relates to a different ethane/oxygen ratio and much lower space velocities: each condition was tested for at least 100 h.

TABLE 1

|  | Example 1A | Example 1B | Example 1C | Example 1D |
|---|---|---|---|---|
| Catalyst | PS7AL2 | PS7AL2 | PS7AL2 | PS7AL2 |
| Reactor geometry | tubular | tubular | tubular | tubular |
| Operating conditions |  |  |  |  |
| $T_{out}$ (° C.) | 828 | 787 | 771 | 768 |
| p (bar) | 1.319 | 1.22 | 1.21 | 1.23 |
| GHSV (NL/kg/h) | 603.600 | 389.300 | 380.600 | 402.400 |
| $C_2H_6/O_2$ | 2.08 | 2.27 | 2.38 | 2.48 |
| $H_2/O_2$ | 2.185 | 2.000 | 2.000 | 2.000 |
| Performance |  |  |  |  |
| Conversion $C_2H_6$ | 68.7% | 64.0% | 61.3% | 59.0% |
| Conversion $O_2$ | 100% | 100% | 100% | 100% |
| Selectivity $C_2H_4$ | 79.9% | 80.5% | 81.3% | 81.9% |
| Selectivity CO | 7.0% | 6.8% | 6.3% | 6.0% |
| Selectivity $CO_2$ | 1.8% | 2.6% | 2.2% | 2.2% |
| Selectivity $CH_4$ | 5.5% | 5.3% | 4.8% | 4.7% |
| Selectivity $C_2H_2$ | 1.5% | 1.6% | 1.3% | 1.2% |
| Selectivity $C_3$ | 1.6% | 1.4% | 1.5% | 1.4% |
| Selectivity $C_{4>}$ | 2.7% | 1.8% | 2.6% | 2.6% |
| Tot. selectivity | 100.0% | 100.0% | 100.0% | 100.0% |

TABLE 2

|  | Ex. 2A | Ex. 2B | Ex. 2C | Ex. 2D | Ex. 2E | Ex. 2F |
|---|---|---|---|---|---|---|
| Catalyst | PS7SN4 | PS7SN1 | PS7SN 3 | PS7SN4 | PS7SN3 | PS7SN3 |
| Reactor geometry | tubular | tubular | tubular | tubular | tubular | tubular |
| Operating conditions | | | | | | |
| $T_{out}$ (° C.) | 874 | 878 | 837 | 822 | 818 | 804 |
| p (bar) | 1.21 | 1.46 | 1.34 | 1.24 | 1.34 | 1.32 |
| GHSV (NL/kg/h) | 424.000 | 493.000 | 538.000 | 424.000 | 543.000 | 535.000 |
| $C_2H_6/O_2$ | 2.50 | 2.08 | 2.50 | 3.33 | 2.84 | 3.21 |
| $H_2/O_2$ | 2.50 | 1.04 | 2.00 | 3.33 | 2.5 | 2.82 |
| Performance | | | | | | |
| Conversion $C_2H_6$ | 60.4% | 73.4% | 65.2% | 31.9% | 49.1% | 39.3% |
| Conversion $O_2$ | 100% | 100% | 100% | 100% | 100% | 100% |
| Selectivity $C_2H_4$ | 80.4% | 82.1% | 83.4% | 84.3% | 86.0% | 89.0% |
| Selectivity CO | 9.4% | 8.5% | 5.6% | 5.8% | 4.3% | 2.9% |
| Selectivity $CO_2$ | 0.7% | 0.4% | 0.3% | 0.4% | 0.3% | 0.2% |
| Selectivity $CH_4$ | 5.5% | 6.5% | 4.8% | 3.9% | 4.2% | 3.3% |
| Selectivity $C_2H_2$ | 1.1% | 0.9% | 1.3% | 0.2% | 0.7% | 0.6% |
| Selectivity $C_3$ | 1.9% | 0.6% | 1.6% | 2.3% | 1.7% | 1.2% |
| Selectivity $C_{4>}$ | 1.0% | 1.0% | 3.0% | 3.1% | 2.8% | 2.8% |
| Tot. selectivity | 100.0% | 100.0% | 100.0% | 100.0% | 100.0% | 100.0% |

TABLE 3

| | Example 3A | Example 3B | | Example 3C |
|---|---|---|---|---|
| Catalyst | PS7SN1 | PS7SN1 | Catalyst | |
| Reactor Geometry | conical | conical | Reactor geometry | conical |
| Operating conditions | | | Operating conditions | |
| $T_{out}$ (° C.) | 933 | 944 | $T_{out}$ (° C.) | 755 |
| P (bars) | 1.43 | 1.38 | P (bars) | 1.3 |
| GHSV (NL/kg/h) | 552,000 | 475,000 | GHSV (NL/kg/h) | 42.300 |
| $O_2/C$ | 3.205 | 3.205 | $O_2/C$ | 0.25 |
| $H_2/O_2$ | 2.00 | 1.00 | $(CO + H_2O)/O_2$ | 2.50 |
| Performance | | | Performance | |
| Conversion $C_2H_6$ | 35.2% | 34.4% | Conversion $C_2H_6$ | 50.6% |
| Conversion $O_2$ | 100% | 100% | Conversion $O_2$ | 100% |
| Selectivity $C_2H_4$ | 85.5% | 81.9% | Selectivity $C_2H_4$ | 84.4% |
| Selectivity CO | 5.7% | 8.3% | Selectivity CO | 0.0% |
| Selectivity $CO_2$ | 0.3% | 1.0% | Selectivity $CO_2$ | 6.7% |
| Selectivity $CH_4$ | 4.8% | 5.1% | Selectivity $CH_4$ | 4.3% |
| Selectivity $C_2H_2$ | 1.0% | 1.4% | Selectivity $C_2H_2$ | 1.0% |
| Selectivity $C_3$ | 1.7% | 1.6% | Selectivity $C_3$ | 1.4% |
| Selectivity $C_{4>}$ | 1.0% | 0.7% | Selectivity $C_{4>}$ | 2.2% |
| Tot. Selectivity | 100.0% | 100.0% | Tot. Selectivity | 100.0% |

The invention claimed is:

1. A catalytic system for a catalytic partial oxidation reaction of a hydrocarbon, comprising:
   one or more nitrides selected from the group consisting of $Co_3N$, $Cr_2N$, $Fe_4N$, $Mn_4N$, MoN, WN, VN, $Si_3N_4$, a Si—N—B system, a Si—B—N—C system, an oxynitride and mixtures thereof; and
   a combination of at least two metals deposited on said nitrides,
   wherein said combination is selected from the group consisting of Pt—Sn, Pt—Ga, Pt—Cu and Pt—Sn—Ga.

2. The catalytic system according to claim 1, comprising from 0.05 to 15% by weight of said combination of metals.

3. A process for the production of an olefin from a gaseous paraffinic hydrocarbon, comprising:
   partially oxidizing said hydrocarbon with a gas containing molecular oxygen in the presence of a catalytic system according to claim 1, to obtain said olefin,
   wherein said hydrocarbon has 2 to 6 carbon atoms.

4. The process according to claim 3, wherein the partial oxidation is effected at a temperature ranging from 450 to 1000° C., at a pressure ranging from 1 to 15 Atm and a space velocity ranging from 5000 to 800000 $h^{-1}$.

5. The process according to claim 3, wherein the partial oxidation is carried out using a reactor in which a gas inlet zone and a catalytic zone either have a tubular shape or a sand-glass shape or a truncated-conical shape.

6. The process according to claim 5, wherein a stream of oxygen, air or enriched air and a fuel not having the function of directly producing an olefin is sent into the gas inlet zone and a gaseous stream of paraffinic hydrocarbon is sent into the catalytic zone.

7. The process according to claim 5, wherein in the tubular-shaped or sand-glass shaped or truncated-conical shaped reactor, the catalyst fillings are differentiated so as to have two or three catalytic beds in series.

8. The process according to claim 7, wherein a catalytic bed upstream consists of Pt deposited on said nitride and a catalytic bed down-stream consists of Pt, Sn and Ga deposited on said nitride.

9. The process according to claim 7, wherein a catalytic bed upstream consists of Pt and Cu deposited on said nitride and a catalytic bed down-stream consists of Pt, Sn and Ga deposited on said nitride.

10. The process according to claim 7, wherein a catalytic bed upstream consists of Pt deposited on said nitride, an intermediate catalytic bed consists of Pt and Sn deposited on said nitride, and a catalytic bed downstream consists of Pt, Sn and Ga deposited on said nitride.

11. The process according to claim 7, wherein a catalytic bed upstream consists of Pt and Cu deposited on said nitride, an intermediate catalytic bed consists of Pt, Sn and Bi deposited on said nitride, and a catalytic bed downstream consists of Pt, Sn and Ga deposited on said nitride.

12. The process according to claim 7, wherein a catalytic bed upstream consists of Pt deposited on said nitride, an intermediate catalytic bed consists of Pt and Sn deposited on said nitride, and a catalytic bed downstream consists of Pt, Sn and Sb deposited on said nitride.

13. The process according to claim 7, wherein a catalytic bed upstream consists of Pt and Cu deposited on said nitride, an intermediate catalytic bed consists of Pt, Sn and Cr deposited on said nitride, and a catalytic bed downstream consists of Pt, Sn and Ga deposited on said nitride.

14. The process according to claim 7, wherein a catalytic bed upstream consists of Pt and Sn deposited on said nitride, an intermediate catalytic bed consists of Pt and Sn deposited on said nitride, and a catalytic bed downstream consists of Pt, Sn and Ga deposited on said nitride.

15. A process for the production of an olefin from a gaseous paraffinic hydrocarbon, comprising:
   partially oxidizing said hydrocarbon with a gas containing molecular oxygen in the presence of a catalytic system according to claim 1;
   wherein said oxidation is effected at a temperature ranging from 450 to 1000° C., at a pressure ranging from 1 to 15 Atm and at a space velocity ranging from 5000 to 800000 $h^{-1}$ in a reactor in which a gas inlet zone and a catalytic zone either have a tubular shape or a sand-glass shape or a truncated-conical shape;
   wherein a stream of oxygen, air or enriched air and a fuel not having the function of directly producing an olefin is sent into the gas inlet zone and a gaseous stream of paraffinic hydrocarbon is sent into the catalytic zone.

16. The process according to claim 6, wherein the fuel not having the function of directly producing olefin is selected from the group consisting of i) natural gas, ii) synthesis gas, iii) hydrogen and iv) a mixture of hydrogen and CO.

17. The process according to claim 15, wherein the fuel not having the function of directly producing an olefin is selected from the group consisting of i) natural gas, ii) synthesis gas, iii) hydrogen and iv) a mixture of hydrogen and CO.

* * * * *